United States Patent [19]

Finger

[11] Patent Number: Plant 5,361

[45] Date of Patent: Dec. 4, 1984

[54] KALANCHOE PLANT NAMED SINGAPUR

[75] Inventor: Hermann Finger, Wiesmoor, Fed. Rep. of Germany

[73] Assignee: Wiesmoor-Gartnerei und Baumschule GmbH, Wiesmoor, Fed. Rep. of Germany

[21] Appl. No.: 477,932

[22] Filed: Mar. 23, 1983

[51] Int. Cl. ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Koch

[57] ABSTRACT

A new and distinct cultivar of Kalanchoe named Singapur having vigorous growth habit and free branching, highly floriferous, with numerous cherry colored flowers formed at every shoot, excellent keeping quality, and its suitability for production in 8 to 15 cm. pots.

1 Drawing Figure

The present invention relates to a new and distinctive cultivar of Kalanchoe plant, botanically known as Kalanchoe, and referred to by the cultivar name Singapur.

The new cultivar was referred to during the breeding and selection process by the designation WG 1, and is a product of a planned breeding program. The basic objective of the breeding program was to create a new Kalanchoe cultivar having vigorous growth, short flowering time, and excellent quality foliage and flowers.

The new cultivar was originated from a cross made in a controlled breeding program in Wiesmoor, West Germany. The female, or seed parent was a patented cultivar designated Solferinopurpur, disclosed in U.S. Plant Pat. No. 3,843. The male, or pollen parent was a cultivar designated Pollux, disclosed in U.S. Plant Pat. No. 4,816.

Singapur was discovered and selected by me as a flowering plant within the progency of the stated cross in a controlled environment in Wiesmoor, West Germany. Asexual reproduction of the new cultivar by stem cuttings, as performed by me at Wiesmoor, West Germany, has demonstrated that the combination of characteristics as herein disclosed for the new cultivar are firmly fixed and are retained through successive generations of asexual reproduction.

Singapur has not been observed under all possible environmental conditions. The phenotype may vary significantly with variations in environment such as temperature, light intensity and day length. The following observations, measurements and values describe the new cultivar as grown in Wiesmoor, West Germany, under greenhouse conditions which closely approximate those generally used in commercial practice.

The following traits have been repeatedly observed and are determined to be basic characteristics of Singapur, which in combination distinguish this Kalanchoe as a new and distinct cultivar:

1. Singapur was selected especially for the excellent keeping quality of the foliage and the flowers.
2. Freely branching, with or without pinching.
3. Growth is more vigorous than that of either parent.
4. Proper scheduling makes Singapur suitable for production in 8 to 15 cm. pots.
5. To reduce peduncle elongation after flower initiation, plants can be treated with Alar or B9.

6. Singapur is highly floriferous, with numerous cherry colored flowers formed at every shoot.
7. Flowering time is 10 weeks in summer and 14 weeks in winter after start of short days.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color alues are taken under artifical light conditions approximately at noon in Wiesmoor, West Germany.

Botonaical classification: Kalanchoe cv. Singapur.

Parentage:

*Male parent.*—Pollux.

*Female parent.*—Solferinopurpur.

PROPAGATION

The new cultivar holds its distinguishing characteristics through successive propagations by leaf cuttings and by division of shoots.

Type cutting: Short tip cutting, with stems up to 2 cm. long.

Time to root: 9 Days at 21° C. summer. 13 Days at 21° C. winter.

Rooting habit: Many very fine roots, fibrous.

PLANT DESCRIPTION

Form: Short, compact, upright. Growing and scheduling practices can produce small plants in 8 cm. pots up to larger plants in 15 cm. pots.

Habit of growth: Relatively fast for this type of plant. Generally, shoots are formed at every node.

Foliage description: Leaves simple, opposite, generally symmetrical, tending to be slightly folded upward from the main vein.

1. *Size.*—Average full grown leaves of flowering plants in 10 cm. pots are 100 mm. long and 70 mm. wide.
2. *Shape.*—Ovate to elliptic, apex and base obtuse.
3. *Texture.*—Glabrous, coriaceous, succulent.
4. *Margin.*—Sinuate to crenate.
5. *Color.*—Young foliage top side, yellow green 147A, under side, yellow green 147B. Mature foliage top side yellow green 147A, under side green 137A.

FLOWERING DESCRIPTION

Flowering habit: Inflorescence of each shoot is formed by dichotomous branching, starting with opening of terminal flowers of main axis, followed by terminal flowers of the side branches. Opening of new buds will continue for two months or more. Individual flowers last two weeks or more after opening.

Natural flowering season: January. Flowering time under controlled daylength at 20° C. in summer is 10 weeks; in winter at 20° C., 14 weeks. Flowering time depends on temperature, light intensity and other growing conditions.

Flower buds: Developing to tubular as flower petals mature, sheathed with four green sepals; corolla at maturity 8 mm. long.

1. *Size.*—Up to 11 mm. long.
2. *Shape.*—Generally oblong.
3. *Rate of opening.*—Opening of new buds will continue for two months or more.

Flowers borne: On compound dichasial cymes on strong peduncles. Peduncle length depends on growing and applications of Alar or B9; pedicels up to 6 mm. long.

Quantity of flowers: Highly floriferous. Main axis and side shoots have 100 or more flowers.

Petals:

1. *Shape.*—Nearly round, with top slightly cuspidate.
2. *Color.*—Top side when opening, Red 45B, fading to Red 53C; under side, Red 48B with green strip from apex to top.
3. *Number and size of petals.*—Four, united in corolla, salverform; petals 7 mm. in diameter, total flower diameter 16 mm.

Reproductive organs:

1. *Stamens.*—Eight (8) in number. (a) Anther shape: flat, elliptical, color light brown. (b) Filament color: light green. (c) Pollen color: yellow.
2. *Pistels.*—(a) Stigma shape: flat, crystalline, color greenish white. (b) Style color: light green. (c) Ovaries: 4 celled, 6 mm. long, color yellow green 144A.

DISEASE RESISTANCE

No known Kalanchoe diseases observed to date.

GENERAL OBSERVATIONS

Singapur is extremely tolerant of both high and low temperatures.

I claim:

1. A new and distinct cultivar of Kalanchoe named Singapur, as described and illustrated, and particularly characterized by its vigorous growth habit and free branching, highly floriferous, with numerous cherry colored flowers formed at every shoot, excellent keeping quality, and its suitability for production in 8 to 15 cm. pots.

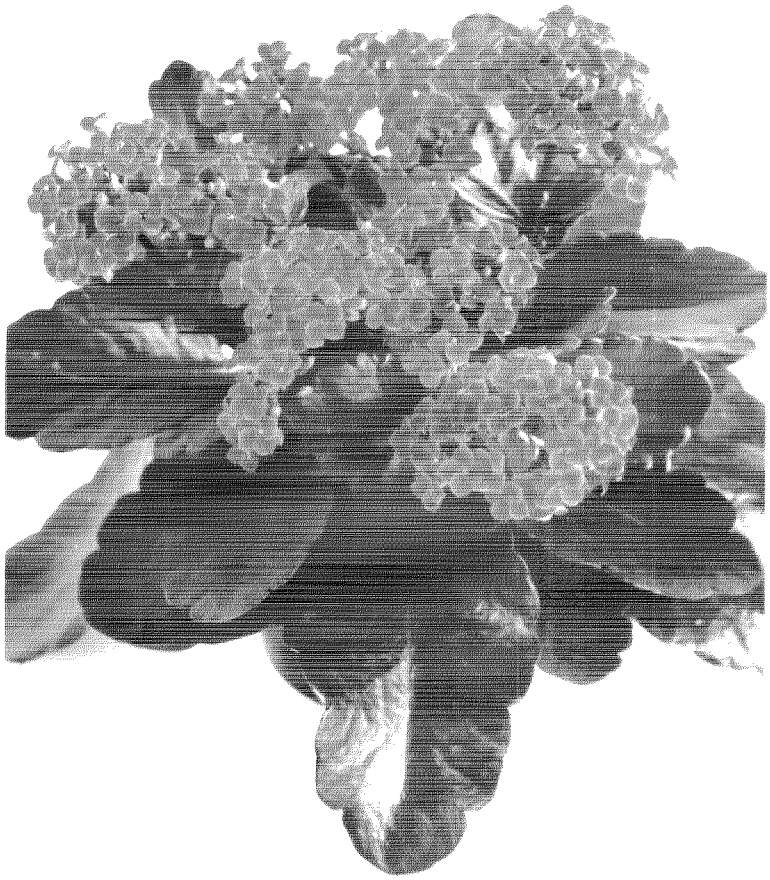

* * * * *